US008951288B2

(12) United States Patent
McGrath et al.

(10) Patent No.: US 8,951,288 B2
(45) Date of Patent: Feb. 10, 2015

(54) DEVICES AND METHODS FOR TREATMENT OF A BONE FRACTURE

(75) Inventors: Timothy J. McGrath, Fremont, CA (US); Ryan Connolly, San Carlos, CA (US)

(73) Assignee: Benvenue Medical, Inc., Santa Clara, CA (US)

( * ) Notice: Subject to any disclaimer, the term of this patent is extended or adjusted under 35 U.S.C. 154(b) by 0 days.

(21) Appl. No.: 13/882,672

(22) PCT Filed: Nov. 9, 2011

(86) PCT No.: PCT/US2011/059916
§ 371 (c)(1),
(2), (4) Date: Jun. 21, 2013

(87) PCT Pub. No.: WO2012/064817
PCT Pub. Date: May 18, 2012

(65) Prior Publication Data
US 2013/0282062 A1    Oct. 24, 2013

Related U.S. Application Data

(60) Provisional application No. 61/411,554, filed on Nov. 9, 2010.

(51) Int. Cl.
*A61B 17/70* (2006.01)
*A61B 17/88* (2006.01)
(52) U.S. Cl.
CPC ......... *A61B 17/7097* (2013.01); *A61B 17/7094* (2013.01); *A61B 17/8852* (2013.01)
USPC .......................................................... 606/246
(58) Field of Classification Search
USPC ..................... 606/246, 279; 623/17.11–17.16
See application file for complete search history.

(56) References Cited

U.S. PATENT DOCUMENTS

| 4,834,069 A | 5/1989 | Umeda |
| 4,898,577 A | 2/1990 | Badger et al. |

(Continued)

FOREIGN PATENT DOCUMENTS

| DE | 19710392 | 1/1999 |
| FR | 2913331 | 9/2008 |

(Continued)

OTHER PUBLICATIONS

International Search Report and Written Opinion for PCT/US2011/059916 dated Feb. 17, 2012.

(Continued)

*Primary Examiner* — Pedro Philogene
*Assistant Examiner* — David Comstock
(74) *Attorney, Agent, or Firm* — Cook Alex Ltd.

(57) ABSTRACT

An implant and method are provided for treating a fractured bone. The implant includes a generally elongated member having a first configuration for introduction between body tissue layers and a second configuration in-situ having a curved portion. The generally elongated member includes a plurality of alternating projections and slots and a plurality of occlusions wherein each of the occlusions is positioned between adjacent projections. The occlusions at least partially occlude an upper and/or lower side of the associated slot. Additionally, the projections may be configured to overlap each other when the implant is deployed in the second configuration. The occlusions and/or overlapping projections promote improved fluid flow and dispersion through the deployed implant and into the fractured bone. Also provided are methods for using the implant to treat a bone fracture.

27 Claims, 6 Drawing Sheets

(56) References Cited

U.S. PATENT DOCUMENTS

| | | |
|---|---|---|
| 4,904,261 A | 2/1990 | Dove et al. |
| 5,228,441 A | 7/1993 | Lundquist |
| 5,285,795 A | 2/1994 | Ryan et al. |
| 5,322,505 A | 6/1994 | Krause et al. |
| 5,454,827 A | 10/1995 | Aust et al. |
| 5,669,926 A | 9/1997 | Aust et al. |
| 5,681,263 A | 10/1997 | Flesch |
| 5,695,513 A | 12/1997 | Johnson et al. |
| 5,848,986 A | 12/1998 | Lundquist et al. |
| 5,851,212 A | 12/1998 | Zirps et al. |
| 6,012,494 A | 1/2000 | Balazs |
| 6,073,051 A | 6/2000 | Sharkey et al. |
| 6,364,828 B1 | 4/2002 | Yeung et al. |
| 6,419,641 B1 | 7/2002 | Mark et al. |
| 6,425,887 B1 | 7/2002 | McGuckin et al. |
| 6,491,626 B1 | 12/2002 | Stone et al. |
| 6,656,178 B1 | 12/2003 | Veldhuizen et al. |
| 6,749,560 B1 | 6/2004 | Konstorum et al. |
| 6,780,151 B2 | 8/2004 | Grabover et al. |
| 6,805,697 B1 | 10/2004 | Helm et al. |
| 7,048,694 B2 | 5/2006 | Mark et al. |
| 7,276,062 B2 | 10/2007 | McDaniel et al. |
| 7,608,083 B2 | 10/2009 | Lee et al. |
| 7,637,905 B2 | 12/2009 | Saadat et al. |
| 2002/0077700 A1 | 6/2002 | Varga et al. |
| 2002/0082584 A1 | 6/2002 | Rosenman et al. |
| 2002/0107573 A1 | 8/2002 | Steinberg |
| 2003/0199979 A1 | 10/2003 | McGuckin, Jr. |
| 2003/0208136 A1 | 11/2003 | Mark et al. |
| 2004/0034343 A1 | 2/2004 | Gillespie et al. |
| 2004/0133124 A1 | 7/2004 | Bates et al. |
| 2005/0216018 A1 | 9/2005 | Sennett |
| 2006/0036273 A1 | 2/2006 | Siegal |

FOREIGN PATENT DOCUMENTS

| | | |
|---|---|---|
| WO | WO 93/04634 | 3/1993 |
| WO | WO 00/67650 | 11/2000 |
| WO | WO 00/67651 | 11/2000 |
| WO | WO 01/10316 | 2/2001 |
| WO | WO 0115639 | 3/2001 |
| WO | WO 02/17824 | 3/2002 |
| WO | WO 03/028587 | 4/2003 |
| WO | WO 03/101308 | 12/2003 |
| WO | WO 2004/062505 | 7/2004 |
| WO | WO 2004/082526 | 9/2004 |
| WO | WO 2006/072941 | 7/2006 |
| WO | WO 2007/022194 | 2/2007 |
| WO | WO 2008/084479 | 7/2008 |
| WO | WO 2008084479 A2 | 7/2008 |
| WO | WO 2008/103781 | 8/2008 |
| WO | WO 2008103781 A2 | 8/2008 |
| WO | WO 2009/019669 | 2/2009 |
| WO | WO 2010/013188 | 7/2009 |
| WO | WO 2009/113032 | 9/2009 |

OTHER PUBLICATIONS

U.S. Appl. No. 60/557,246, filed Mar. 29, 2004.

DEVICES AND METHODS FOR TREATMENT OF A BONE FRACTURE

CROSS REFERENCE TO RELATED APPLICATIONS

This application is the U.S. National Stage of International Patent Application No. PCT/US2011/059916, filed Nov. 9, 2011, which claims the benefit of U.S. Provisional Application Ser. No. 61/411,554, filed Nov. 9, 2010, all of the above of which are hereby incorporated herein by reference in their entireties.

TECHNICAL FIELD

The present disclosure generally relates to apparatus and methods employed in minimally invasive surgical procedures and more particularly to various aspects of apparatus and methods for separating and/or supporting tissue layers, especially in the spine.

BACKGROUND ART

A variety of physical conditions involve two tissue surfaces that, for diagnosis or treatment of the condition, need to be separated or distracted or maintained in a separated, spaced-apart condition from one another. Such separation or distraction may be to gain exposure to selected tissue structures, to apply a therapeutic pressure to selected tissues, to return or reposition tissue structures to a more normal or original anatomic position and form, to deliver a drug or growth factor, to alter, influence or deter further growth of select tissues, to carry out other diagnostic or therapeutic procedures either solely or in combination with one or more of the above procedures. Depending on the condition being treated, the tissue surfaces may be opposed or contiguous and may be bone, skin, soft tissue, or a combination thereof.

Figures 1, 2, 3, 4:
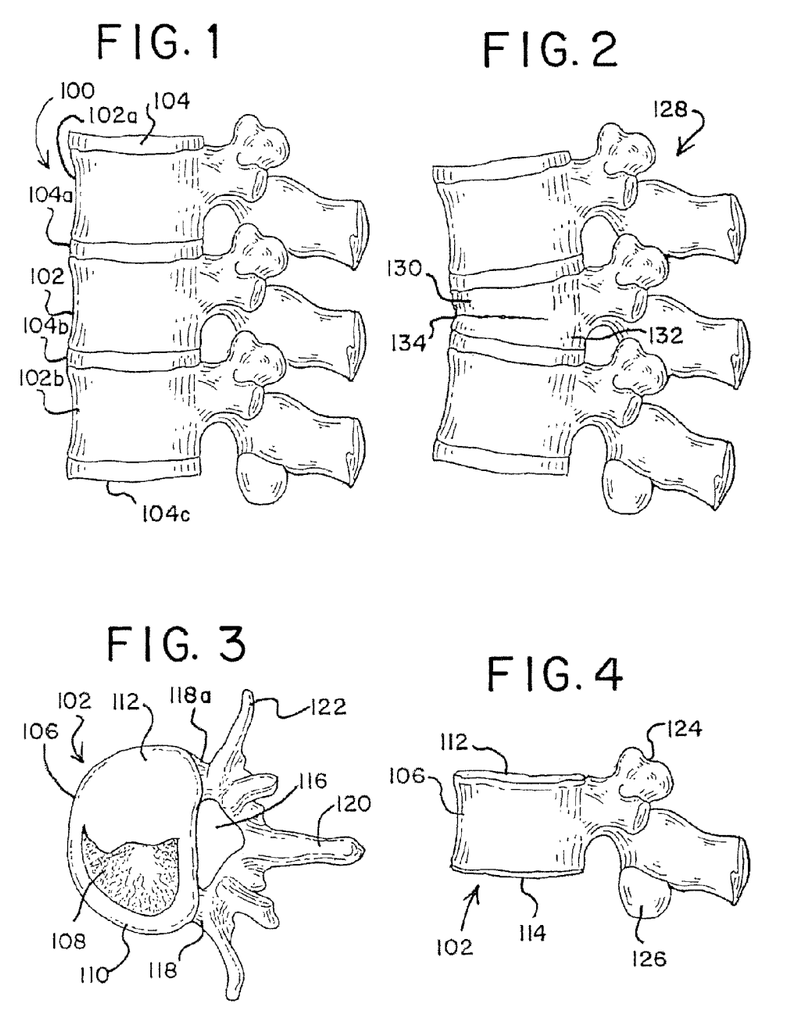
FIG. 1 is a partial side view of a normal human vertebral column.
FIG. 2 is comparable to FIG. 1, but shows a vertebral compression fracture in one of the vertebral bodies.
FIG. 3 is a top view of a vertebral body with an endplate partially removed.
FIG. 4 is a side view of the vertebral body of FIG. 3.

One such condition that occurs in the orthopedic field is a vertebral compression fracture. FIG. 1 illustrates a section of a healthy vertebral (spinal) column, generally designated as 100, without injury. In contrast, FIG. 2 shows a vertebral column 128 having a vertebral compression fracture 134.

The vertebral column 100 of FIG. 1 includes adjacent vertebrae 102, 102a and 102b and intervertebral disks 104, 104a, 104b and 104c separating the adjacent vertebrae. FIGS. 3 and 4 illustrate in more detail a normal vertebra and its attributes. The vertebra, generally designated as 102, includes a vertebral body 106 that is roughly cylindrically and comprised of inner cancellous bone 108 surrounded by a cortical rim 110, which is comprised of a layer of cortical compact bone. The cortical rim 110 can be weakened by osteoporosis and may be fractured due to excessive movement or loading or even due to routine physical activity or simply due to aging and bone loss. The body 106 of the vertebra is capped at the top by a superior endplate 112 and at the bottom by an inferior endplate 114 (FIG. 4), made of a cartilaginous layer. To the posterior (or rear) of the vertebral body 106 is the vertebral foramen 116, which contains the spinal cord (not shown). On either side of the vertebral foramen 116 are the pedicles 118 and 118a, which lead to the spinous process 120. Other elements of the vertebra include the transverse process 122, the superior articular process 124, and the inferior articular process 126.

The damaged vertebral column 128 of FIG. 2 has a vertebral body 130 of a vertebra 132 suffering from a compression fracture 134. The vertebral body 130 suffering from the compression fraction 134 becomes typically wedge shaped and reduces the height of both the vertebra 132 and vertebral column 128 on the anterior (or front) side. As a result, this reduction of height can affect the normal curvature of the vertebral column 128 and can lead to discomfort or pain.

Vertebral compression fractures affect a significant part of the population, and add significant cost to the health care system. As shown in FIG. 2, a vertebral compression fracture is a crushing or collapsing injury to one or more vertebrae. Vertebral fractures are generally, but not exclusively, associated with osteoporosis, metastasis, and/or trauma. Osteoporosis reduces bone density, thereby weakening bones and predisposing them to fracture. The osteoporosis-weakened vertebrae can collapse during normal activity and are also more vulnerable to injury from shock or other forces acting on the spine. In severe cases of osteoporosis, routine physical motion and actions as simple, for example, as bending forward can be enough to cause a vertebral compression fracture. Vertebral compression fractures are the most common type of osteoporotic fractures according to the National Institute of Health.

One technique used to treat vertebral compression fractures is injection of bone filler into the fractured vertebral body. This procedure is commonly referred to as percutaneous vertebroplasty. Vertebroplasty involves injecting bone filler (for example, bone cement, allograph material or autograph material) into the collapsed vertebra to stabilize and strengthen the crushed bone.

In vertebroplasty, physicians typically use one of two surgical approaches to access thoracic and lumbar vertebral bodies: transpedicular or extrapedicular. The transpedicular approach involves the placement of a needle or wire through the pedicle into the vertebral body, and the physician may choose to use either a unilateral access or bilateral transpedicular approach. The extrapedicular technique involves an entry point through the posterolateral corner of the vertebral body.

Regardless of the surgical approach, the physician generally places a small diameter guide wire or needle along the path intended for the bone filler delivery needle. The guide wire is advanced into the vertebral body under fluoroscopic guidance to the delivery point within the vertebra. The access channel into the vertebra may be enlarged to accommodate the delivery tube. In some cases, the delivery tube is placed directly into the vertebral body and forms its own opening. In other cases, an access cannula is placed over the guide wire and advanced into the vertebral body. After placement, the cannula is replaced with the delivery tube, which is passed over the guide wire or pin. In both cases, a hollow needle or similar tube is placed through the delivery tube into the vertebral body and used to deliver the bone filler into the vertebra.

In this procedure, the use of lower viscosity bone filler and higher injection pressures tend to disperse the bone filler throughout the vertebral body. However, such procedures can dramatically increase the risk of bone filler extravasation from the vertebral body. The difficulty of controlling or stopping bone filler flow into injury-sensitive areas increases as the required pressure increases. Thus, caution must be taken to prevent extravasation, with the greatest attention given to preventing posterior extravasation because it may cause spinal cord trauma. Physicians typically use repeated fluoroscopic imaging to monitor bone filler propagation and to avoid flow into areas of critical concern. If a foraminal leak results, the patient may require surgical decompression and/ or suffer paralysis.

Kyphoplasty is another type of treatment for vertebral fractures. Kyphoplasty is a vertebral fracture treatment that uses one or two balloons, similar to angioplasty balloons, to attempt to reduce the fracture and, perhaps, restore some vertebral height prior to injecting the bone filler. One or two balloons are typically introduced into the vertebra via bilateral transpedicular cannula. The balloons are inflated to reduce the fracture. After the balloon(s) are deflated and removed, leaving a relatively empty cavity, bone cement is injected into the vertebra. In theory, inflation of the balloons may restore some vertebral height. However, in practice it is difficult to consistently attain meaningful and predictable height restoration. The inconsistent results may be due, in part, to the manner in which the balloon expands in a compressible media, such as the cancellous tissue within the vertebrae, and the structural orientation of the trabecular bone within the vertebra, although there may be additional factors as well.

In response to these disadvantages, the treatment of vertebral compression fractures was advanced by methods of inserting an implant into a fractured vertebral body to distract the superior and inferior endplates, thereby restoring proper height to the vertebral body. Typically, bone filler or bone cement is also injected into the vertebral body after the implant has been inserted.

Figures 5, 6:
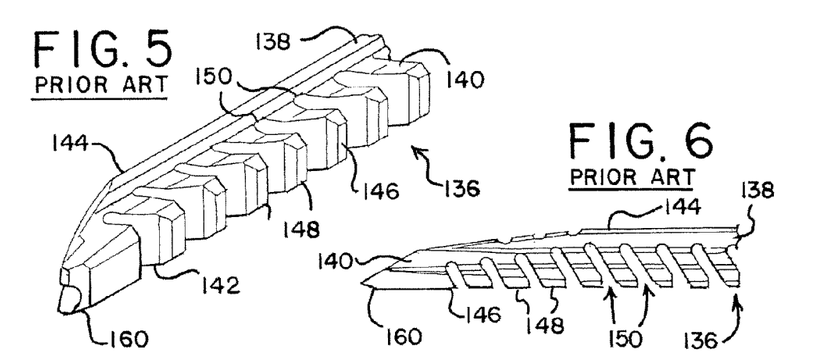
FIG. 5 is a perspective view of a distraction device according to known design.
FIG. 6 is a top plan view of the distraction device of FIG. 5.

A challenge in the use of a posterior procedure to install spinal prosthesis devices is that a device large enough to contact the end plates and expand the space between the endplates of the vertebral body must be inserted through a limited space. FIGS. 5-13 generally illustrate a known implant or distraction device 136 which is suitable for implantation into a fractured vertebral body. The distraction device, generally at 136 (only a distal portion of which is shown in FIGS. 5 and 6), is comprised of an elongated member 138. As illustrated in FIGS. 5 and 6, the distraction device 136 has a generally rectangular cross-sectional shape defined by a top surface 140, a bottom surface 142, and opposed first and second sidewalls 144 and 146. The elongated member 138 includes a plurality of spaced apart, laterally extending projections or teeth 148, with a recess or slot 150 defined between adjacent projections 148. The distraction device 136 is made of a rigid material and is substantially rigid or incompressible in a first dimension or direction between the top surface 140 and the bottom surface 142, and substantially flexible in a second dimension or direction that is generally perpendicular to the first dimension and extends along the length of the distraction device 136. The distraction device 136 is typically made from biocompatible materials that are suitable for long term implantation into human tissue in the treatment of degenerative tissue, trauma or metastatic conditions or where a tissue distraction device is needed.

FIGS. 7-11 illustrate one method of deploying the distraction device 136 over a guide wire 152, wherein the distraction device 136 and the guide wire 152 are deployed incrementally from a delivery cannula 154. The distraction device 136 includes a center bore or passageway that accepts the guide wire 152 for slidably mounting the distraction device 136 onto the guide wire 152. Prior to deployment (i.e., while present in the delivery cannula 154), the distraction device 136 is constrained by the shape of the cannula and guidewire and typically has a generally linear pre-deployed configuration, as illustrated in FIGS. 5 and 6.

Figures 7, 8, 9, 10:
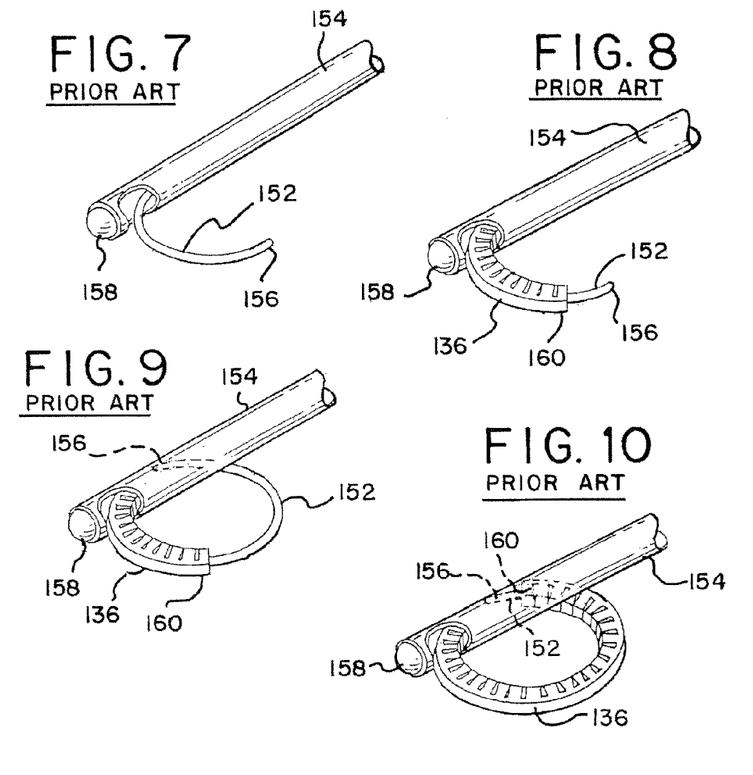
FIG. 7 is a perspective view of a guide wire being advanced from a cannula according to a know method.
FIG. 8 is a perspective view of a distraction device of FIG. 5 being advanced over the guide member of FIG. 7.
FIG. 9 is a perspective view of the guide member of FIG. 7 being further advanced out of the cannula.
FIG. 10 is a perspective view of the distraction device of FIG. 8 being further advanced over the guide member of FIG. 9.
Figures 11, 12:
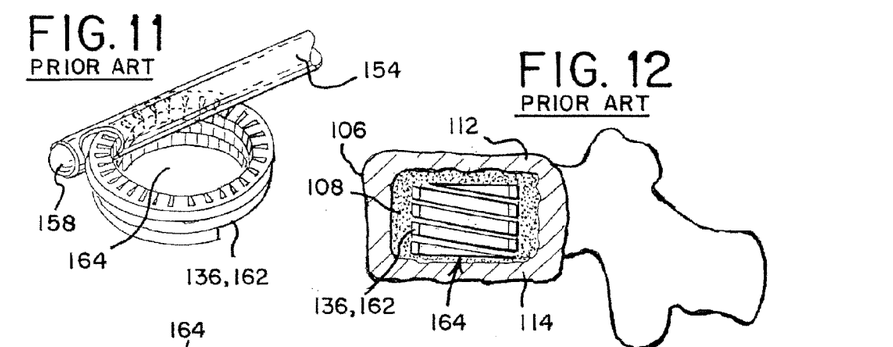
FIG. 11 is a perspective view of a distraction device in a coiled configuration and forming a support structure.
FIG. 12 is a cross-sectional view of a vertebral body shown with the distraction device of FIG. 5 defining a support structure therein.

Referring to FIG. 7, a distal portion 156 of the guide wire 152 is advanced out of the distal end portion 158 of the delivery cannula 154 and into a treatment site (i.e., a vertebral body 106, as shown in FIG. 12). At least the coil-shaped distal portion 156 of the guide wire 152 is preferably made of a shape memory material, such as a nitinol or a polymer having shape memory characteristics, so that the guide wire 152 can be deformed into a generally straight configuration within the delivery cannula 154 prior to or during deployment of the guide wire 152 into the treatment site. When the distal end portion 156 of the guide wire 152 is advanced out of the delivery cannula 154, and is no longer constrained by the cannula, the guide wire resiliently returns from its straight constrained configuration to its predisposed coiled configuration.

Next, the distraction device 136 is advanced over the curved distal portion 156 of the guide wire 152 (FIG. 8) while the guide wire 152 is held in place with respect to the delivery cannula 154. The distraction device 136 may be advanced along the coiled distal portion 156 of the guide wire 152 by pressing a pusher or plunger member in the delivery cannula 154 (not illustrated) distally. The distraction device 136 has sufficient flexibility to follow along the contour of the guide wire 152. The curvature is such that the teeth or projections 148 of the distraction device 136 remain spaced apart and do not abut, leaving a passageway therebetween for the injection of bone filler or cement following insertion.

The guide wire 152 is then further advanced out of the delivery cannula 154 (FIG. 9) while maintaining the distraction device 136 in place relative to the delivery cannula 154. This has the effect of extending the distal portion 156 of the guide wire 152 farther beyond the distal end 160 of the distraction device 136. Thereafter, the distraction device 136 is then further advanced over the guide wire 152 (FIG. 10), for example to bring the distal end 160 of the distraction device 136 into the proximity of the distal-most end of the guide wire 152. The incremental deployment of the distraction device 136 via the alternating advancement of the guide wire 152 and then the distraction device 136 continues until the distraction device 136 defines a coiled support structure 162 with the desired height (FIGS. 11 and 12). Alternatively, the guide wire 152 may be fully deployed, followed by the distraction device 136 being advanced out of the delivery cannula 154 and along the guide wire 152 until the support structure 162 attains the desired height. They may also be able to be advanced simultaneously.

Hence, when deployed into a vertebral body 106, the distraction device 136 follows the curved path defined by the guide wire 152 to define a spiral or helical structure 162 that extends substantially vertically within the vertebral body and serves to actively separate or support (or both) the opposed endplates 112 and 114 of the vertebral body 106, as shown in FIG. 12, for example, by engaging or pressing against the opposed end plates. The support structure 162 typically defines a helical configuration with a tight pitch forming an essentially hollow cylinder. Each coil, turn, or winding may have little or no spacing between adjacent windings, although some limited spacing may be employed. Because the distraction device 136 is therefore substantially rigid in the first dimension between the top and bottom surfaces 140 and 142 in this deployed configuration, the support structure 162 provides a relatively stiff support along the axis of the spine and leaves an internal volume or core of relatively undisturbed cancellous bone inside the hollow cylindrical structure, as well as largely undisturbed cancellous bone between the structure and the cortical rim.

After the support structure 162 has been formed, if desired, the guide wire 152 can be removed from the deployed distraction device 136. Alternatively, the guide wire 152 can remain in place within the distraction device 136 to further strengthen and stabilize the support structure 162. In such usage, the proximal portion of the guide wire 152 is severed from the remainder of the guide wire 152. In either situation, no void or cavity is formed in the vertebral body, and cancellous bone is not compressed or compacted, as in Kyphoplasty.

Figures 13, 14, 16:
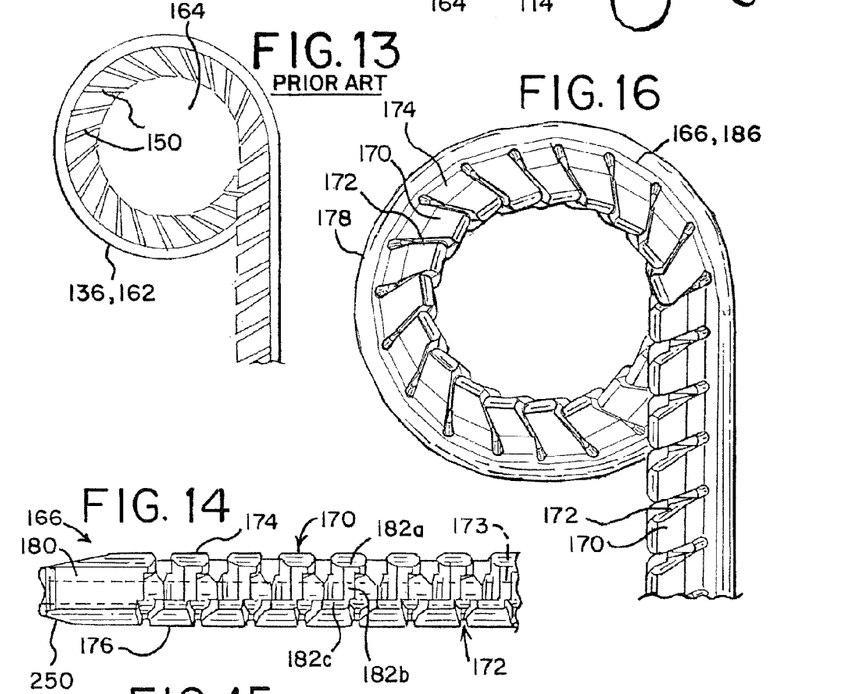
FIG. 13 is a top plan view of the support structure of FIG. 12.
FIG. 14 is a side elevational view of a distraction device according to an aspect of the present disclosure.
FIG. 16 is a top plan view of the distraction device of FIG. 14 defining a support structure.

As mentioned above, the support structure 162 includes or defines an innerspace, core, or resident volume 164 (FIGS. 11 and 13). As used herein, "resident volume" refers generally to a structural characteristic of a support structure or deployed distraction device. The resident volume is a volume that is generally defined by the distraction device when it is in the deployed configuration, and as illustrated is generally a cylindrical-shaped volume extending between the end plates and located within the windings of the distraction structure.

With the distraction device 136 deployed in the vertebral body 106, a flavorable bone filler or other material may be injected into the vertebral body 106 in any of a variety of ways. For example, if the guide wire 152 has been retracted from the center bore of the distraction device 136, flowable filler material (e.g., bone cement bone augmentation material or filler, or other diagnostic and/or therapeutic material) may be injected through the center bore of the distraction device. As noted above, the teeth or projections 148 preferably do not abut in either the insertion or deployed configuration and remain spaced apart to allow flowable material to flow into the cancellous bone within the resident volume via the slots 150 of the distraction device 136. The flowable material preferably interdigitates with the cancellous bone tissue 108 located within the resident volume 164, and the tubular configuration of the support structure 162 retards extravasation of filler material out the resident volume 164 either anteriorly, posteriorly, or laterally. More detail regarding distraction systems of this type can be found in U.S. Patent Application Publication No. 2008/0234827 to Schaller et al., which is incorporated herein by reference.

While the above devices and methods represent a significant advance in treatment of vertebral compression fractures, advances have continued, particularly in terms of controlling and limiting the spread of bone filler or other flowable material injected into the vertebral body to augment the implant. For example, the slots 150 of the distraction device 136 in the deployed configuration (FIG. 13) remain open in both the radially inward and axially vertical directions. Such slots 150 allow filler material to be injected inwardly into the resident volume 164, but also allows an amount of filler material to be injected in other directions, such as upwardly and downwardly in the direction of the axis of the spine which could potentially lead to some filler material unintentionally flowing into space outside of the structure and toward the intervertebral space. Further, due to the size and configuration of the slots 150, it can be a challenge to reliably deliver filler material to the distal end of the support structure 162, which can affect the uniformity with which the filler material is injected into the resident volume 164. There may also be, as mentioned above, a potential for cement "bypass," wherein the filler material flows around the upper and lower ends of the structure, into the surrounding cancellous bone tissue.

SUMMARY OF INVENTION

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, an implant comprises a generally elongated member and has a first configuration for introduction between body tissues layers and a second configuration in-situ having a curved portion. The generally elongated member is defined by a plurality of alternating projections and slots and a plurality of relatively thin webs. Each web is positioned between adjacent projections and at least partially occludes an upper or lower side of the associated slot. The webs may be located in each slot or in only a selected number of slots or in a preselected arrangement, e.g., in every second or third slot or other arrangements. The slots are configured to allow the implant to define the curved portion and each web is configured to at least partially occlude the upper and/or lower side of the associated slot in the curved portion.

In another aspect, a method is provided for inserting an implant into the body. The method involves providing an implant defined by a plurality of alternating projections and slots. A treatment site in the body is accessed and a distal end of the implant is advanced into the treatment site. The slots allow the implant to define a curved portion while at least a portion of the upper or lower sides of the slots are occluded in the curved portion of the implant.

In yet another aspect, an implant comprises a generally elongated member having a first configuration for introduction between body tissues layers and a second configuration in-situ having a curved portion. The generally elongated member is defined by a plurality of alternating projections and slots. Each projection comprises a first section, a second section longitudinally offset from the first section, and a third section longitudinally offset from the first and second sections. The slots allow the projections to move toward each other to define the curved portion, while the adjacent projections remain spaced apart in the curved portion.

In another aspect, a method is provided for inserting an implant into the body. The method involves providing an implant defined by a plurality of alternating projections and slots. A treatment site in the body is accessed and a distal end of the implant is advanced into the treatment site while simultaneously moving adjacent projections in the treatment site toward each other to define a curved portion in which at least a portion of one of the projections faces and is spaced from at least a portion of an adjacent projection.

In yet another aspect, an implant comprises a generally elongated member having a first configuration for introduction between body tissues layers and a second configuration in-situ having a curved portion. The generally elongated member is defined by a plurality of alternating projections and slots, with each projection comprising a first section, a second section longitudinally offset from the first section, and a third section longitudinally offset from the first and second sections. The generally elongated member further includes a plurality of relatively thin webs, with each web being positioned between adjacent projections and at least partially occluding an upper or lower side of the associated slot. The adjacent projections are configured to move toward each other to define the curved portion and each web is configured to at least partially occlude the upper and lower sides of the associated slot in the curved portion.

In another aspect, a method is provided for inserting an implant into the body. The method involves providing an implant defined by a plurality of alternating projections and slots. A treatment site in the body is accessed and a distal end of the implant is advanced into the treatment site. Adjacent projections in the treatment site are moved toward each other to define a curved portion in which at least a portion of one of the projections faces and is spaced from at least a portion of an adjacent projection and at least a portion of the upper or lower sides of the slots are occluded in the curved portion of the implant.

DESCRIPTION OF EMBODIMENTS

The embodiments disclosed herein are for the purpose of facilitating a description of the present subject matter. They are exemplary only, and the subject matter herein may be embodied in various forms. Therefore, specific details disclosed herein are not to be interpreted as limiting the subject matter as defined in the accompanying claims.

The devices and methods of the present invention provide multiple features of spinal implants, such as distraction devices, deployment systems, and filler material injection tools, which may be used by themselves, with each other or, alternatively, in combination with known devices and/or methods.

As used herein, the terms "distraction device" and "support structure" are intended to have a general meaning and are not limited to devices that only actively separate tissue layers, only support tissue layers or only both actively separate and support tissue layers. For example, a distraction device/support structure in general can be used to actively separate layers of tissue and then be removed after such separation, or the distraction device/support structure could be used to support layers of tissue that have been previously separated by a different device. Alternatively, the distraction device/support structure can be used to actively separate the layers of tissue and remain in place to support the layers of tissue in order to maintain such separation. Unless more specifically used herein, "distraction device" and "support structure" encompass any and all of these.

It should also be understood that various embodiments of devices, systems, and methods of the present subject matter are illustrated for purposes of explanation in the treatment of vertebral compression fractures. However, in its broader aspects, the various features of the present disclosure are not limited to these particular applications and may be used in connection with other tissue layers, such as non-vertebral bones requiring the restoration of their original height, although they have particular utility and benefit in treatment of vertebral conditions.

Figure 15:
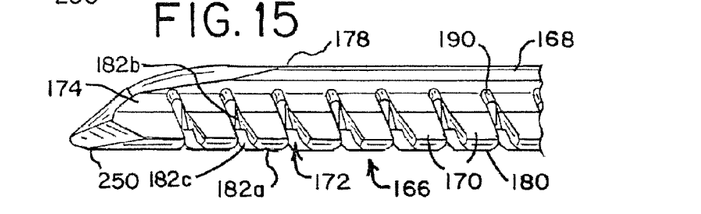
FIG. 15 is a top plan view of the distraction device of FIG. 14.

FIGS. 14-18 illustrate an example of an implant or distraction device 166 according to an aspect of the present disclosure, with only a portion of the distraction device 166 being shown. The distraction device, generally at 166, has a generally rectangular cross-section or other suitable cross-sectional shape and comprises an elongated member 168, as shown in FIG. 15, with a plurality of projections or elements 170 spaced along the length of the elongated member 168 and extending generally laterally therefrom. Adjacent projections 170 are separated by recesses or slots 172. The illustrated elongated member 168 has general top and bottom surfaces 174 and 176 (FIG. 14) (top and bottom referring to the surfaces in the "as implanted" configuration) and opposed first (or outer) and second (or inner) sidewalls 178 and 180, respectively (FIG. 15) (also in the "as implanted" configuration). More particularly, the first or outer sidewall 178 is continuous and preferably without interruption, while the second or inner sidewall 180 is defined in part by outer end surfaces of the projections 170. The distraction device 166 is made of substantially incompressible material and is relatively rigid in a first dimension or direction between its top and bottom surfaces 174 and 176 and substantially flexible in a second dimension or direction that is generally perpendicular to the first dimension and extends along the length of the distraction device 166 to allow curving or bending of the device in the direction illustrated in FIG. 16.

The distraction device 166 may be made from biocompatible materials that are suitable for long term implantation into human tissue in the treatment of degenerative tissue, trauma or metastatic conditions or where a tissue distraction device is needed. Suitable biocompatible materials include calcium phosphate, tricalcium phosphate, hydroxyapatite, polyether ether ketone (PEEK), nylon, and nitinol (NiTi). The material may be solid or porous to allow for tissue ingrowth, and may elute therapeutic or growth enhancing agents. One of the advantages of using biological or biocompatible material to treat vertebral compression fractures is that these elements are more natural like. However, other materials could be used and still be within the scope of the present invention. The distraction device 166 is advantageously (but not necessarily) formed as a unitary structure and may be formed into the illustrated configuration by any of a number of suitable methods, including molding or machining (or a combination) the illustrated features into the unitary structure (e.g., by employing a laser or other cutting means) to arrive at the illustrated shape.

Figure 17:
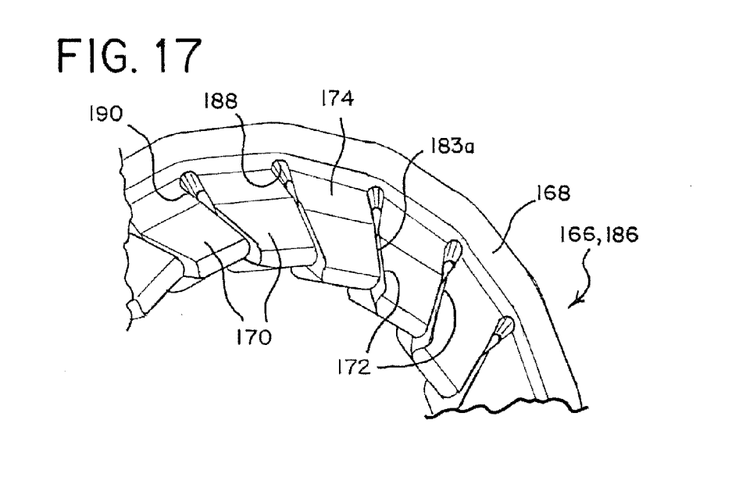
FIG. 17 is a top detail view of a curved or coiled portion of the support structure of FIG. 16.
Figure 18:
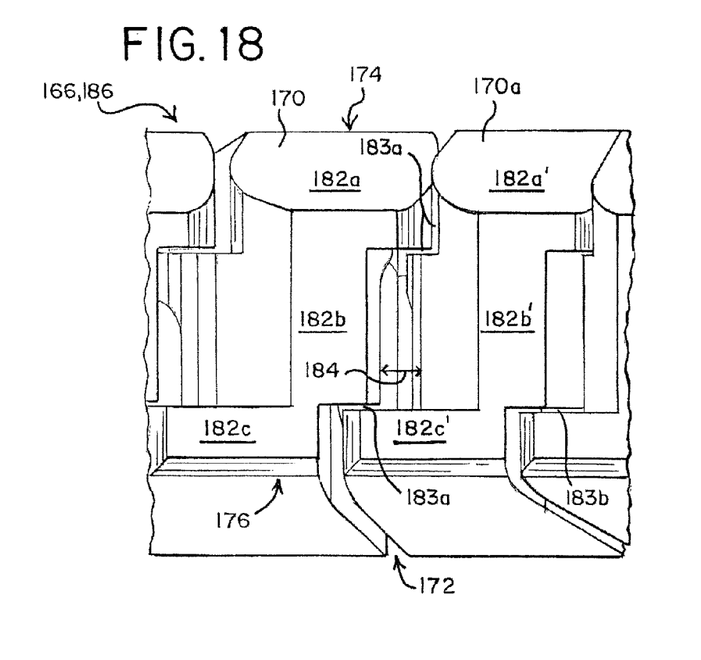
FIG. 18 is a side detail view of a curved or coiled portion of the support structure of FIG. 16.

The distraction device 166 of FIGS. 14-18 is employed in a general manner similar to the distraction device 136 of FIGS. 5 and 6, in that it is preferably introduced into a treatment site in a linear configuration (FIGS. 14 and 15), but moved into a curved or coiled support structure 186 (FIG. 16) for short or long-term deployment or implantation within the treatment site. However, in contrast to the known design, the distraction device 166 of FIGS. 14-18 employs an "overlapping slot" design, in which the adjacent projections remain spaced apart and in non-contacting or non-abutting relationship in the coiled position (FIG. 16), and the slots define a preferential flow path(s) for bone filler or other material to flow radially inwardly toward and into the resident volume and provide resistance to substantial flow through the slots in a vertical direction. More specifically, the facing surfaces of adjacent projections act as louvers and form high-resistance labyrinth flow paths when the distal end of the distraction device 166 is deployed in a curved or coiled configuration (FIGS. 16-18). For example, FIG. 6 shows that the slots 150 of the prior art implant 136 are generally defined by vertical cuts from the top surface 140 to the bottom surface 142. On account of this design, each projection 148 has a generally uniform cross-section when viewed from above, and the slots between them provide flow paths, radially inwardly and vertically. On the other hand, the facing surfaces of the projections 170 of the distraction device 166 of FIGS. 14-18 are multi-planar (as shown in FIGS. 14 and 18), with each illustrated projection 170 being defined by a plurality of steps forming sections 182a-182c.

Referring to FIGS. 14 and 18, the illustrated sections 182a-182c may be described as generally rectangular elements or structures, such as prisms or cuboids, arranged in a vertical stack or array, with the first section 182a being located above the second section 182b and the second section 182b being located above the third section 182c in the orientation of FIGS. 14 and 18. More particularly, in the illustrated embodiment, each first section 182a defines a portion of the top surface 174 of the distraction device 166, each third section 182c defines a portion of the bottom surface 176 of the distraction device 166, and each second section 182b defines a midsection which spans the space between the associated first section 182a and third section 182c. At least a portion of the second section 182b is longitudinally offset from the first section 182a and at least a portion of the third section 182c is longitudinally offset from the first and second sections 182a and 182b, resulting in each projection 170 having a non-uniform horizontal cross-section (see FIGS. 15 and 17). Although illustrated with three sections, more or fewer may be used, and the number of sections and/or shapes may vary along the length of the implant.

Each illustrated projection 170 includes a generally longitudinal through-hole or channel 173 (shown in broken lines in FIG. 14). The through-holes of adjacent projections 170 may be substantially aligned in order to receive a guide wire and/or to jointly form or act as a fluid flow lumen when the distraction device 166 is deployed and the guide wire removed. The guide wire may be provided according to the foregoing description of the known guide wire 152 of FIG. 7 and cooperates with the distraction device 166 in generally the same manner as it does with the known distraction device 136 to deploy the distraction device 166 to a treatment site.

The manner in which adjacent projections 170 and 170' overlap when the distraction device 166 has been curved or coiled to define a support structure 186 is best illustrated in FIGS. 17 and 18. In the curved or coiled support structure 186, a portion of each first section 182a (i.e., the portion which extends proximally beyond the proximal edge of the associated second section 182b) overlays or overlaps a portion of an adjacent second section 182b' (i.e., the portion which extends distally beyond the distal edge of the associated first section 182a'), forming a narrow spacing or clearance 183a between them.

Similarly, a portion of each third section 182c' (i.e., the portion which extends distally beyond the distal edge of the associated second section 182b') overlays or overlaps a portion of an adjacent second section 182b (i.e., the portion which extends proximally beyond the proximal edge of the associated third section 182c), forming a narrow spacing or clearance 183b between them.

The separation between the overlapping sections of adjacent projections 170 may be relatively small (e.g., approximately 0.002" in one embodiment) compared to the size of the gap 184 between adjacent second sections 182b and 182b' (approximately 0.008" in the same embodiment). By such overlapping action, contact-less labyrinth passageways are formed between adjacent projections 170 and 170'. The contact-less labyrinth passageways provide substantial resistance to the flow of bone filler material, e.g., cement, and greatly limits vertical or cranial extravasation of bone filler material. Preferably, such passageways substantially, but not entirely, reduce or eliminate such fluid flow in the vertical direction. On the contrary, a limited and controlled amount of vertical or cranial fluid flow is preferably but not necessarily allowed, while the larger gaps 184 provide passageways of much less resistance to direct more fluid toward the center of the resident volume encircled by the support structure 186, thereby establishing a preferential fluid flow path arrangement.

Allowing a controlled amount of vertical or cranial extravasation may be advantageous for a number of reasons. Vertically flowing injection fluid may help bind and seal the coils of the deployed support structure 186 together, providing a stronger support structure 186. However, when compared to known distraction devices, the vertical extravasation is preferably reduced and more controlled, and of a quantity preferably limited to what is useful for the purpose described above. In other aspects, the fluid passageways may provide sufficiently high flow resistance that there is essentially no flow in the vertical direction even though the projections remain spaced apart and non-abutting. For example, in some prior art devices, approximately 20-30% of the fluid injected through the deployed device may extravasate vertically whereas, in some embodiments according to the present disclosure, there will be only approximately 10% or less vertical extravasation. The remainder of the flowable fluid will continue through the fluid flow lumen of the support structure 186 and/or be directed into the resident volume defined by the support structure 186 via the preferential flow paths formed by the radially inward facing gaps 184. Directing fluid toward the center of the support structure 186 through the several radial gaps 184 may be advantageous in encouraging interdigitation of the fluid with the cancellous bone contained in the resident volume.

To allow the distraction device 166 to move from a straight configuration to a curved or coiled one, the slots 172 preferably have a minimum longitudinal gap length, such that the adjacent projections 170 may move toward each other to reduce the size of the slots 172 as described above, which results in the curved and, ultimately, coiled support structure 186 shown in FIGS. 16-18. While the overlapping action of adjacent projections 170 (as previously described) helps to narrow the slots 172, there may be a small portion of the vertex of each slot 172 (i.e., the portion at and adjacent to the inner edge or root 188 of the slot 172, as shown in FIG. 17) which remains open in the coiled configuration of FIGS. 16-18 and may provide an unwanted avenue for bone filler passage. To better control the vertical or cranial extravasation of fluid at these locations, each slot 172 may be provided with one or more occlusions such as webs 190, which are best illustrated in FIG. 17. FIG. 17 only shows webs 190 at or adjacent to the top surface 174 of the distraction device 166, but there may also be webs 190 at other locations, such as at or adjacent to the bottom surface 176 of the distraction device 166. On, alternatively, the webs may be at the top side or bottom side but not both. The discussion herein of webs applies equally to webs positioned at the top and bottom surfaces 174 and 176 of the distraction device 166 and also applies to webs disposed in any other location of the distraction device 166.

The illustrated webs 190 are flaps or strips of material located in the vertex region of the slots 172 when the distraction device is deployed and, in the illustrated embodiment, extend between the projections 170 on either side of the associated slot 172. The webs 190 may be relatively thin, for example, having a thickness that is approximately 0.005" in one embodiment or approximately one-tenth the thickness of the distraction device 166 itself or less. In the illustrated embodiment, the webs 190 are positioned at or adjacent to the roots 188 of the slots 172, which may be advantageous in providing webs capable of acting as a shield or cover which overlays and closes at least a portion of the opening, thereby limiting cranial extravasation of an injected fluid from the lumen of the support structure 186 through the slots 172. While it may be advantageous to limit vertical flow from the slots 172, a small degree of vertical flow may be desirable to allow the injection fluid to seal together the adjacent projections 170, further strengthening the support structure 186. The webs 190 may be provided at both inferior and superior ends or sides of the slots 172 or at just one end to limit flow in a single direction only. Also, the webs may be provided between only certain teeth, such as those at the proximal and distal end portions of the distraction device that occupy the uppermost and/or lowermost windings to reduce bypass, and not provided between other teeth between the proximal and distal end portions.

The design thus described (which may include one or more of the foregoing features) effectively forms a lumen in the distraction device 166 such that cement (or other injection fluids) will flow from proximal to distal ends in the curved or coiled support structure 186, all while the adjacent projections preferably remain in a spaced-apart, non-abutting relationship, with preferential flow radially inwardly into the defined resident volume, and limited or no flow vertically. As compared to known designs, the labyrinth passageways and webs 190 of the distraction device 166 of FIGS. 14-18 provide a more continuous, uninterrupted lumen or flow path when in the deployed, coiled state, while providing a preferential bone filler or cement flow direction toward the center of the resident volume encircled by the deployed distraction device 166. However, the labyrinth passageways and webs 190 also preferably allow for a limited, controlled amount of vertical flow to better seal adjacent coils of the deployed support structure 186 to each other. Hence, distraction devices according to the present disclosure are configured to allow for improved fluid flow therethrough and, hence, improved treatment of a fractured vertebral body or other treatment site, with improved flow control of bone filler, such as cement or other material that may be introduced through the support structure.

As for the particular means for injecting fluid into and through the lumen of the distraction device 166, known devices and methods may be used, such as providing a rigid injection needle, positioning its distal end at the proximal end of the distraction device 166, and then injecting the fluid.

Alternatively, flexible injection needles may be used to allow the injection needle to track along the curved lumen of a coiled support structure. Examples of such flexible injection needles may be found in PCT/US11/55207 filed on Oct. 7, 2011 which is incorporated herein by reference, Now that certain components have been described, an exemplary treatment method will be described in conjunction with FIGS. 19-27, although it should be understood that other methods using the treatment devices described herein may also be employed without departing from the scope of the present disclosure.

Figures 19, 20, 21, 22:
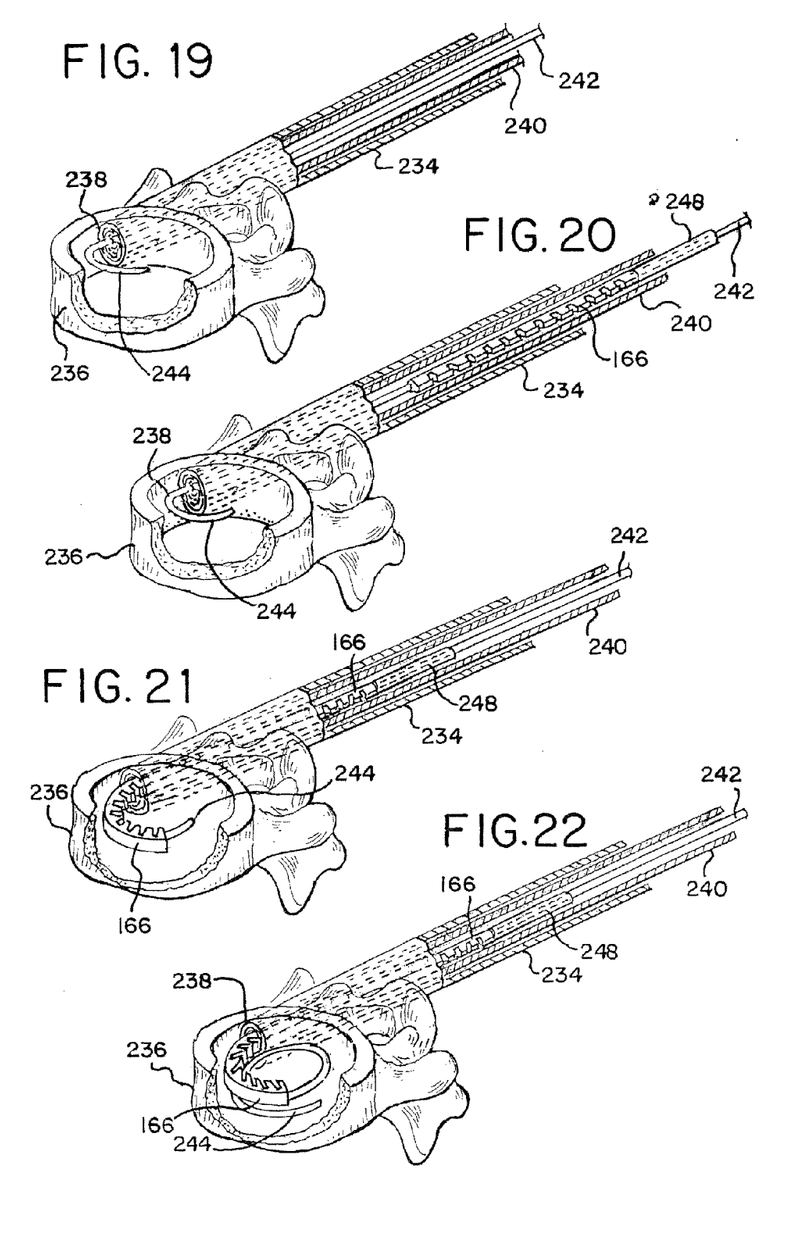
FIG. 19 is a partial cross-sectional perspective view of one embodiment of a delivery system with a guide wire partially deployed.
FIG. 20 is a partial cross-sectional perspective view of the delivery system of FIG. 19 employing a pusher for advancing the distraction device over the guide wire.
FIG. 21 is a partial cross-sectional perspective view of the delivery system of FIG. 20 with the pusher advanced distally and the distraction device partially advanced over a coiled section of the guide wire.
FIG. 22 is a partial cross-sectional perspective view of the delivery system of FIG. 21 with the guide wire further advanced.

Referring to FIG. 19, an introducer sheath or working cannula 234 is introduced through the back of a patient while the patient is lying in a prone position. Fluoroscopic guidance using a biplane imaging system for better visualization of the spine may be used to help guide the delivery system to the desired location. The working cannula 234 can be introduced into a vertebral body 236 using, for example, a transpedicular access approach. Once the working cannula 234 is inserted through an access port 238 and is in the desired position, a delivery cannula 240 is inserted into the working cannula 234 and a guide wire 242 is advanced forward through the delivery cannula 240. Alternatively, the delivery cannula 240 may be inserted into the vertebral body 236 without an introducer sheath.

As in the prior art system, at least the distal portion 244 of the guide wire 242 may be made of a shape memory material that has an initial or free state in the shape of a curve or coil. When the guide wire 242 is present within the delivery cannula 240, the cannula 240 constrains the guide wire 242 into a generally elongated linear configuration, allowing an easy and minimally invasive deployment of the guide wire 242 into the treatment site. Because of the shape memory properties, the guide wire 242 will return to its curve- or coil-shaped free state once the constraint is removed, i.e., as the distal portion 244 of the guide wire 242 exits the distal end portion of the delivery cannula 240 and enters the vertebral body 236. The guide wire 242 can be advanced through the delivery cannula 240 manually or with the aid of an advancing mechanism or plunger.

After the guide wire 242 has achieved the partially deployed configuration of FIG. 21, the distraction device 166 of FIG. 14 is advanced over the proximal portion of the guide wire 242 (i.e., the straightened portion of the guide wire 242 constrained by the delivery cannula 240). The distraction device 166 assumes a generally linear configuration while it is positioned within the delivery cannula 240. The distraction device 166 may be moved along the guide wire 242 by a pusher member 248 (FIG. 21). As the pusher member 248 is advanced, it contacts the distraction device 166 and advances it forward or distally over the guide wire 242. A drive mechanism (not shown) can be employed to advance the pusher member 248.

Referring to FIG. 21, as the distraction device 166 is advanced forward (distally) over the guide wire 242, the guide wire 242 guides the distraction device 166 through the delivery cannula 240 and into the vertebral body 236. The distal end 250 of the distraction device 166 can be tapered, ramped or otherwise shaped if desired (FIG. 15) to aid in passing through tissue (e.g., cancellous bone tissue). The slots 172 of the distraction device 166 add flexibility and facilitate the curving of the distraction device 166 so that it follows the contour of the guide wire 242.

Figures 23, 24, 25, 26, 27:
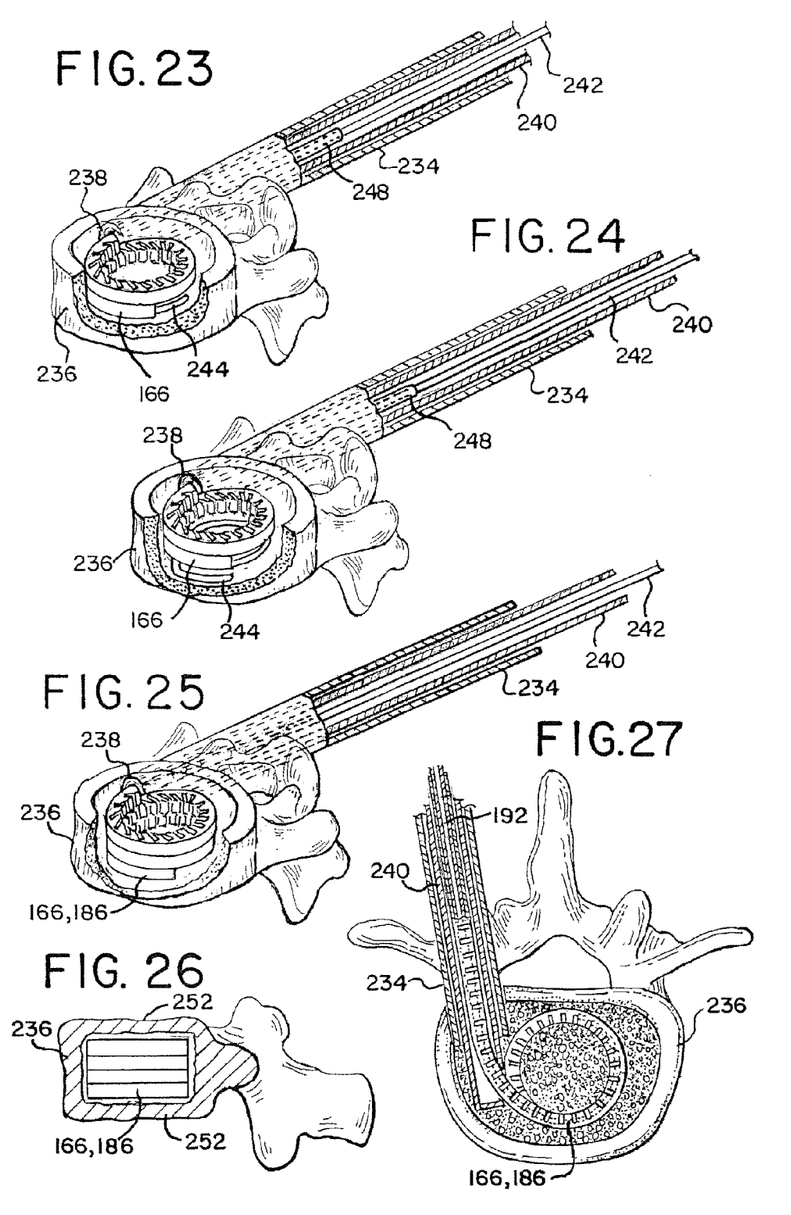
FIG. 23 is a partial cross-sectional perspective view of the delivery system of FIG. 22 with the pusher advanced further distally and the distraction device further advanced over the coiled section of the guide wire.
FIG. 24 is a partial cross-sectional perspective view of the delivery system of FIG. 24 with the guide wire even further advanced.
FIG. 25 is a partial cross-sectional perspective view of the delivery system of FIG. 24 with the with the distraction device substantially advanced over the coiled section of the guide wire.
FIG. 26 is a cross-sectional view of a distraction device forming a support structure within a veterbral body.
FIG. 27 is a top view of a fluid injection device being advanced within a distraction device.

When the distraction device 166 reaches the partially deployed configuration of FIG. 21, the guide wire 242 is then further advanced out of the delivery cannula 240 (FIG. 22) while maintaining the distraction device 166 in place relative to the delivery cannula 240. This has the effect of extending the distal portion 244 of the guide wire 242 farther beyond the distal end of the distraction device 166. Thereafter, the distraction device 166 is then further advanced over the guide wire 242 (FIG. 23) to bring the distal end of the distraction device 166 closer to or into the proximity of the distal-most end of the guide wire 242. The incremental deployment of the distraction device 166 via the alternating advancement of the guide wire 242 and then the distraction device 166 continues (FIGS. 24 and 25) until the distraction device 166 defines a support structure 186 with the desired height (FIG. 26). The physician may check for proper positioning periodically via fluoroscope.

With each formation of an additional coil or winding of the support structure 186, the support structure 186 increases in height. As the support structure 186 increases in height and engages the end plates or tissue adjacent thereto, it distracts and supports the endplates 252 of the vertebral body 236 (FIG. 26), restoring or partially restoring vertebral height and stabilizing the vertebral body 236.

After the distraction device 166 has been deployed to its full height (FIG. 26), the guide wire 242 is retracted from the distraction device 166 and removed from the system. Thereafter, the injection assembly 192, such as one described and illustrated in PCT/US11/55207 incorporated by reference above, can be advanced to (FIG. 27) and through the lumen of the support structure 186. As the injection assembly 192 enters the curved or coiled support structure 186, its flexible distal end tracks along the curves until it reaches the desired location.

With the injection assembly 192 in the desired location, a source of flowable injection fluid (e.g., bone augmenting fluid, such as bone filler, including cement) is connected in fluid flow communication with the proximal end of the injection tube. The injection fluid is injected through the injection tube and exits out of distal parts, e.g., side ports, passes through the radially directed openings 184 of the support structure 186, and enters the resident volume, where it preferably interdigitates with the cancellous bone tissue. The webs 190 and overlapping projections 170 (if provided) better ensure that the injection fluid flows through the lumen of the support structure 186 and preferably out the radially directed openings 184, with only a limited amount of extravasation through the top and/or bottom of the slots 172 of the support structure 186. The presence of the support structure 186 advantageously substantially limits or prevents the injection fluid from entering any other unplanned region of the vertebral body 236, including extravasation into the vicinity of the spinal cord.

The injection tube 192 may either be held stationary while injecting fluid into the treatment site or may be moved with respect to the distraction device 166. In one embodiment, the injection tube is moved proximally with respect to the distraction device 166 (i.e., withdrawn from the distraction device 166) while injecting fluid. By withdrawing the injection tube 192 while injecting fluid into the treatment site, a different fluid dispersion profile can be achieved in the treatment site as compared to the dispersion profile achieved by injecting fluid while maintaining the injection tube in place.

In yet another embodiment, the injection tube 192 may be moved to a location within the distraction device 166 and then held stationary while fluid is injected. When a suitable amount of fluid has been injected for that particular location, the injection tube 194 may be moved to a different location within the distraction device 166 (e.g., by moving the injection tube proximally with respect to the distraction device 166) and then held stationary for a second fluid injection step. This process may be repeated multiple times for a fluid dispersion profile that is comparable to, but different from, the aforementioned simultaneous injection tube 192 movement and fluid injection. For example, the injection tube 192 may be positioned so as to inject fluid at three or more specific locations, such as: (1) at or adjacent to the distal end of the deployed distraction device 166, (2) at or adjacent to the middle of the deployed distraction device 166, and (3) at or adjacent to the proximal end of the deployed distraction device 166. By doing so, fluid will be injected near the inferior and superior endplates of the vertebral body, as well as at a more central location in the resident volume defined by the deployed distraction device 166. Other fluid injection profiles may also be employed without departing from the scope of the present disclosure.

Upon completion of fluid injection, the injection tube 192 is withdrawn from the support structure 186. Thereafter, the working and delivery cannulae 234 and 240 may be removed, while the support structure 186 remains in the vertebral body 236.

The following paragraphs include several examples of devices according to the present disclosure and additional aspects thereof.

A first example of an implant according to the present disclosure includes a generally elongated member having a first configuration for introduction between body tissues layers and a second configuration in-situ having a curved portion. The generally elongated member being defined by a plurality of alternating projections and slots and a plurality of occlusions. Each occlusion being positioned between adjacent projections and at least partially occluding an upper and/or lower side of the associated slot. The slots are configured to allow the implant to define the curved portion and each occlusion is configured to at least partially occlude said upper or lower side of the associated slot in said curved portion.

In one aspect the present disclosure relates to the implant of Example 1 wherein each occlusion extends from one projection to an adjacent projection.

In another aspect the present disclosure relates to the implant of Example 1, alone or in combination with the aspect in the preceding paragraph, wherein the occlusions are positioned at or adjacent to a top surface and/or a bottom surface of the implant.

In yet another aspect the present disclosure relates to the implant of Example 1, alone or in combination with any of the aspects in the two preceding paragraphs, wherein the webs are integrally formed with the projections.

A further aspect the present disclosure relates to the implant of Example 1, alone or in combination with any of the aspects in the three preceding paragraphs, wherein each slot comprises an inner end and an outer end and the occlusion are positioned at the inner ends of the slots.

Yet a further aspect the present disclosure relates to the implant of Example 1, alone or in combination with any of the aspects in the four preceding paragraphs, wherein the occlusions are flexible.

Another aspect the present disclosure relates to the implant of Example 1, alone or in combination with any of the aspects in the five preceding paragraphs, wherein the adjacent projections are configured to define therebetween radial openings in the curved portion.

A first example of a method of inserting an implant into the body, according to the present disclosure includes the step of providing an implant defined by a plurality of alternating projections and slots. The method also includes the steps of accessing a treatment site in the body and advancing a distal end of the implant into the treatment site while simultaneously the slots allow the implant to define a curved portion in the treatment site and at least a portion of the upper or lower sides of the slots are occluded in the curved portion of the implant.

In one aspect the present disclosure relates to the method of Example 1 further comprising advancing the implant toward the treatment site in a generally linear configuration.

In another aspect the present disclosure relates to the method of Example 1, alone or in combination with the aspect in the preceding paragraph, further comprising injecting fluid through the curved portion and into the treatment site.

In yet another aspect the present disclosure relates to the method of Example 1, alone or in combination with any of the aspects in the two preceding paragraphs, further comprising injecting fluid through the curved portion while allowing limited vertical extravasation of fluid through the slots.

A further aspect the present disclosure relates to the method of Example 1, alone or in combination with any of the aspects in the three preceding paragraphs, wherein adjacent projections in the treatment site move toward each other and remain spaced apart in the treatment site to define a coiled portion.

Yet a further aspect the present disclosure relates to the method of Example 1, alone or in combination with any of the aspects in the four preceding paragraphs, wherein said accessing a treatment site in the body includes accessing the interior of a bone.

In yet an even further aspect the present disclosure relates to the method of Example 1, alone or in combination with any of the aspects in the five preceding paragraphs, wherein said accessing a treatment site in the body includes accessing the interior of a vertebral body.

A second example of an implant according to the present disclosure includes a generally elongated member having a first configuration for introduction between body tissues layers and a second configuration in-situ having a curved portion. The generally elongated member being defined by a plurality of alternating projections and slots. Each projection comprises a first section, a second section longitudinally offset from the first section, and a third section longitudinally offset from the first and second section. The slots allow the projections to move toward each other to define the curved portion and adjacent projections remain spaced apart in the curved portion.

In one aspect the present disclosure relates to the implant of Example 2 wherein each projection has a top surface and a bottom surface, the associated first section defining a portion of the top or bottom surface, the associated third section defining a portion of the other of the top or bottom surface, and the second section positioned intermediate the first and third sections.

In another aspect the present disclosure relates to the implant of Example 2, alone or in combination with the aspect in the preceding paragraph, wherein each projection includes a longitudinal through-hole.

In yet another aspect the present disclosure relates to the implant of Example 2, alone or in combination with any of the aspects in the two preceding paragraphs, wherein the through-holes of adjacent projections are substantially aligned.

Still yet another aspect the present disclosure relates to the implant of Example 2, alone or in combination with any of the aspects in the three preceding paragraphs, wherein a portion of each first section faces and is spaced from a portion of the second section of an adjacent projection in the curved portion.

A further aspect the present disclosure relates to the implant of Example 2, alone or in combination with any of the aspects in the four preceding paragraphs, wherein a portion of each third section faces and is spaced from a portion of the second section of an adjacent projection in the curved portion.

Another aspect the present disclosure relates to the implant of Example 2, alone or in combination with any of the aspects in the five preceding paragraphs, wherein the adjacent projections are configured to define therebetween radially inward preferred flow paths in the curved portion.

Yet another aspect the present disclosure relates to the implant of Example 2, alone or in combination with any of the aspects in the six preceding paragraphs, wherein a portion of each first section faces and is spaced from a portion of the second section of an adjacent projection in the curved portion; a portion of each third section faces and is spaced from a portion of the second section of an adjacent projection in the curved portion; the adjacent projections are configured to define therebetween radially inward preferred flow paths; and the size of the radially inward preferred flow paths is greater than the size of the separation between said facing portions.

A second example of a method of inserting an implant into the body, according to the present disclosure includes the step of providing an implant defined by a plurality of alternating projections and slots. The method further includes the steps of accessing a treatment site in the body and simultaneously advancing a distal end of the implant into the treatment site while moving adjacent projections in the treatment site toward each other to define a curved portion in which at least a portion of one of the projections faces and is spaced from at least a portion of an adjacent projection and defines a radially inwardly directed preferential flow path therebetween.

In one aspect the present disclosure relates to the method of Example 2 further comprising advancing the implant toward the treatment site in a generally linear configuration.

In another aspect the present disclosure relates to the method of Example 2, alone or in combination with the aspect in the preceding paragraph, further comprising injecting fluid through the curved portion and into the treatment site.

In yet another aspect the present disclosure relates to the method of Example 2, alone or in combination with any of the aspects in the two preceding paragraphs, further comprising injecting fluid through the curved portion and into the treatment site.

In still yet another aspect the present disclosure relates to the method of Example 2, alone or in combination with any of the aspects in the three preceding paragraphs further comprising injecting fluid through the curved portion and into the treatment site.

A further aspect the present disclosure relates to the method of Example 2, alone or in combination with any of the aspects in the four preceding paragraphs further comprising injecting fluid through the curved portion while allowing limited vertical extravasation of fluid through the slots.

Yet a further aspect the present disclosure relates to the method of Example 2, alone or in combination with any of the aspects in the five preceding paragraphs wherein said moving adjacent projections in the treatment site toward each other includes moving adjacent projections in the treatment site toward each other to define a coiled portion.

Still yet a further aspect the present disclosure relates to the method of Example 2, alone or in combination with any of the aspects in the six preceding paragraphs wherein said accessing a treatment site in the body includes accessing the interior of a bone.

An even further aspect the present disclosure relates to the method of Example 2, alone or in combination with any of the aspects in the seven preceding paragraphs, wherein said accessing a treatment site in the body includes accessing the interior of a vertebral body.

A third example of an implant according to the present disclosure includes a generally elongated member having a first configuration for introduction between body tissues layers and a second configuration in-situ having a curved portion. The generally elongated member being defined by a plurality of alternating projections and slots, each projection comprising a first section, a second section longitudinally offset from the first section, and a third section longitudinally offset from the first and second section. The implant also includes a plurality of relatively thin webs, with each web being positioned between adjacent projections and at least partially occluding an upper or lower side of the associated slot. The adjacent projections are configured to move toward each other to define the curved portion and each web is configured to at least partially occlude said upper and lower sides of the associated slot in said curved portion.

In one aspect the present disclosure relates to the implant of Example 3 wherein each web extends from one projection to an adjacent projection.

In another aspect the present disclosure relates to the implant of Example 3, alone or in combination with the aspect in the preceding paragraph, wherein the webs are positioned at or adjacent to a top surface and/or a bottom surface of the implant.

In yet another aspect the present disclosure relates to the implant of Example 3, alone or in combination with any of the aspects in the two preceding paragraphs, wherein the webs are integrally formed with the projections.

In still yet another aspect the present disclosure relates to the implant of Example 3, alone or in combination with any of the aspects in the three preceding paragraphs, wherein each slot comprises an inner end and an outer end and the webs are positioned at the inner ends of the slots.

A further aspect the present disclosure relates to the implant of Example 3, alone or in combination with any of the aspects in the four preceding paragraphs, wherein the webs are flexible.

An even further aspect the present disclosure relates to the implant of Example 3, alone or in combination with any of the aspects in the five preceding paragraphs, wherein the adjacent projections are configured to define therebetween radial openings in the curved portion.

Another aspect the present disclosure relates to the implant of Example 3, alone or in combination with any of the aspects in the six preceding paragraphs, wherein each projection has a top surface and a bottom surface, the associated first section defining a portion of the top or bottom surface, the associated third section defining a portion of the other of the top or bottom surface, and the second section positioned intermediate the first and third sections.

Yet another aspect the present disclosure relates to the implant of Example 3, alone or in combination with any of the aspects in the seven preceding paragraphs, wherein each projection includes a longitudinal through-hole.

In still yet another aspect the present disclosure relates to the implant of Example 3, alone or in combination the aspect in the preceding paragraph, wherein the through-holes of adjacent projections are substantially aligned.

Even still yet another aspect the present disclosure relates to the implant of Example 3, alone or in combination with any of the aspects in the nine preceding paragraphs, wherein a portion of each first section faces and is spaced from a portion of the second section of an adjacent projection in the curved portion.

An additional aspect the present disclosure relates to the implant of Example 3, alone or in combination with any of the aspects in the ten preceding paragraphs, wherein a portion of each third section faces and is spaced from a portion of the second section of an adjacent projection in the curved portion.

Another aspect the present disclosure relates to the implant of Example 3, alone or in combination with any of the aspects in the eleven preceding paragraphs, wherein a portion of each first section faces and is spaced from a portion of the second section of an adjacent projection in the curved portion; a portion of each third section faces and is spaced from a portion of the second section of an adjacent projection in the curved portion; the adjacent projections are configured to define therebetween radially inward preferred flow paths; and the size of the radially inward preferred flow paths is greater than the size of the separation between said facing portions.

A third example of a method of inserting an implant into the body according to the present disclosure includes the step of providing an implant defined by a plurality of alternating projections and slots. The method further includes the steps of accessing a treatment site in the body and advancing a distal end of the implant into the treatment site while simultaneously moving adjacent projections in the treatment site toward each other to define a curved portion in which at least a portion of one of the projections faces and is spaced from at least a portion of an adjacent projection and occluding at least a portion of the upper or lower sides of the slots in the curved portion of the implant.

In one aspect the present disclosure relates to the method of Example 3 further comprising advancing the implant toward the treatment site in a generally linear configuration.

In another aspect the present disclosure relates to the method of Example 3, alone or in combination with the aspect in the preceding paragraph, further comprising injecting fluid through the curved portion and into the treatment site.

In yet another aspect the present disclosure relates to the method of Example 3, alone or in combination with any of the aspects in the two preceding paragraphs, further comprising injecting fluid through the curved portion while allowing limited vertical extravasation of fluid through the slots.

In still yet another aspect the present disclosure relates to the method of Example 3, alone or in combination with any of the aspects in the three preceding paragraphs, wherein said moving adjacent projections in the treatment site toward each other includes moving adjacent projections in the treatment site toward each other to define a coiled portion.

A further aspect the present disclosure relates to the method of Example 3, alone or in combination with any of the aspects in Example 3 or the preceding paragraph, wherein said accessing a treatment site in the body includes accessing the interior of a bone.

In yet another aspect the present disclosure relates to the method of Example 3, alone or in combination with any of the aspects in Example 3 or the preceding paragraph, wherein said accessing a treatment site in the body includes accessing the interior of a vertebral body.

Another aspect the present disclosure relates to any of the method of Examples 1 to 3, alone or in combination with any of the preceding aspects that include injecting fluid through the curved portion and into the treatment site and/or allowing limited vertical extravasation of fluid through the slots wherein fluid is injected using an injection tube positioned within the implant.

In yet another aspect the present disclosure relates to any of the method of Examples 1 to 3, alone or in combination with the aspect in the preceding paragraph, wherein the fluid is injected as the injection tube is moved toward the distal end of the implant.

In still yet another aspect the present disclosure relates to the aspect in which fluid is injected using an injection tube position within the implant, wherein the fluid is injected as the injection tube is moved away from the distal end of the implant.

Another aspect the present disclosure relates to the aspect in which fluid is injection using an injection tube position within the implant, wherein the injection tube is advanced and/or withdrawn to a plurality of positions within the implant and fluid is injected at each position while the tube is substantially stationary at each position.

Yet another aspect the present disclosure relates to the aspect in which the occlusions are positioned at or adjacent to a top surface and/or a bottom surface of the implant, wherein the occlusion comprises a web.

In still yet another aspect the present disclosure relates the aspect in the preceding paragraph wherein wherein the web comprises a relatively thin web.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

What is claimed:

1. An implant comprising a generally elongated member having a first configuration for introduction between body tissue layers and a second configuration in-situ having a curved portion, the generally elongated member being defined by
   a plurality of alternating projections and slots; and
   a plurality of occlusions, with each occlusion being positioned between adjacent projections and at or adjacent to a root end of an associated slot in said curved portion; and
   wherein the slots are configured to allow the implant to define the curved configuration and each occlusion at least partially occludes said upper or lower side of the associated slot in said curved portion when the elongated member is in the second configuration.

2. The implant of claim 1, wherein each occlusion extends from one projection to an adjacent projection.

3. The implant of claim 1, wherein the occlusions are positioned at or adjacent to a top surface and/or a bottom surface of the implant.

4. The implant of claim 1, wherein the occlusions are integrally formed with the projections.

5. The implant of claim 1, wherein the occlusions are flexible.

6. The implant of claim 1, wherein the adjacent projections are configured to define therebetween radial openings in the curved portion.

7. The implant of claim 1 wherein each projection comprises:
   a first section,
   a second section longitudinally offset from the first section, and
   a third section longitudinally offset from the first and second sections, wherein the slots allow the projections to move toward each other to define the curved portion and adjacent projections remain spaced apart in the curved portion.

8. The implant of claim 7, wherein each projection has a top surface and a bottom surface, the associated first section defining a portion of the top or bottom surface, the associated third section defining a portion of the other of the top or bottom surface, and the second section positioned intermediate the first and third sections.

9. The implant of claim 7, wherein each projection includes a longitudinal through-hole.

10. The implant of claim 9, wherein the through-holes of adjacent projections are substantially aligned.

11. The implant of claim 7, wherein a portion of each first section faces and is spaced from a portion of the second section of an adjacent projection in the curved portion.

12. The implant of claim 7, wherein a portion of each third section faces and is spaced from a portion of the second section of an adjacent projection in the curved portion.

13. The implant of claim 7, wherein the adjacent projections are configured to define therebetween radially inward preferred flow paths in the curved portion.

14. The implant of claim 7, wherein
   a portion of each first section faces and is spaced from a portion of the second section of an adjacent projection in the curved portion;
   a portion of each third section faces and is spaced from a portion of the second section of an adjacent projection in the curved portion;
   the adjacent projections are configured to define therebetween radially inward preferred flow paths; and
   the size of the radially inward preferred flow paths is greater than the size of the separation between said facing portions.

15. The implant of claim 1 wherein the occlusion comprises a web.

16. The implant of claim 15 wherein the web comprises a relatively thin web.

17. A method of inserting an implant into the body, the implant defined by a plurality of alternating projection and slots, the method comprising:

accessing a treatment site in the body; and advancing at least a distal end of the implant into the treatment site while the slots allow the implant to define a curved portion in the treatment site and at least a portion of the upper or lower sides of the slots are occluded in the curved portion of the implant.

18. The method of claim 17, further comprising advancing the implant toward the treatment site in a generally linear configuration.

19. The method of claim 17, further comprising injecting fluid through the curved portion and into the treatment site.

20. The method of claim 19 wherein fluid is injected using an injection tube positioned within the implant.

21. The method of claim 20 wherein the fluid is injected as the injection tube is moved toward the distal end of the implant.

22. The method of claim 20 wherein the fluid is injected as the injection tube is moved away from the distal end of the implant.

23. The method of claim 20 wherein the injection tube is advanced and/or withdrawn to a plurality of positions within the implant and fluid is injected at each position while the tube is substantially stationary at each position.

24. The method of claim 17, further comprising injecting fluid through the curved portion while allowing limited vertical extravasation of fluid through the slots.

25. The method of claim 17, wherein adjacent projections in the treatment site move toward each other and remain spaced apart in the treatment site so as to allow the implant to define a coiled portion.

26. The method of claim 17, wherein said accessing a treatment site in the body includes accessing the interior of a bone.

27. The method of claim 17, wherein said accessing a treatment site in the body includes accessing the interior of a vertebral body.

* * * * *